(12) United States Patent
Tabandeh et al.

(10) Patent No.: US 10,864,050 B2
(45) Date of Patent: Dec. 15, 2020

(54) METHOD AND SYSTEM FOR GUIDING USER POSITIONING OF A ROBOT

(71) Applicant: THINK SURGICAL, INC., Fremont, CA (US)

(72) Inventors: Saleh Tabandeh, Fremont, CA (US); Joel Zuhars, Fremont, CA (US); Daniel Patrick Bonny, Fremont, CA (US); Timothy Pack, Fremont, CA (US); Randall Hanson, Fremont, CA (US); Michael Hoppe, Fremont, CA (US); Nathan A. Netravali, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

(21) Appl. No.: 16/078,336

(22) PCT Filed: Feb. 27, 2017

(86) PCT No.: PCT/US2017/019746
§ 371 (c)(1),
(2) Date: Aug. 21, 2018

(87) PCT Pub. No.: WO2017/147596
PCT Pub. Date: Aug. 31, 2017

(65) Prior Publication Data
US 2019/0069962 A1 Mar. 7, 2019

Related U.S. Application Data

(60) Provisional application No. 62/300,234, filed on Feb. 26, 2016.

(51) Int. Cl.
A61B 34/32 (2016.01)
A61B 34/20 (2016.01)
(Continued)

(52) U.S. Cl.
CPC .............. *A61B 34/32* (2016.02); *A61B 34/00* (2016.02); *A61B 34/10* (2016.02); *A61B 34/20* (2016.02);
(Continued)

(58) Field of Classification Search
CPC ... A61B 34/25; A61B 34/20; A61B 2034/254; A61B 34/30; A61B 34/32; A61B 34/37;
(Continued)

(56) References Cited

U.S. PATENT DOCUMENTS 5,086,401 A 2/1992 Glassman et al.
5,824,085 A * 10/1998 Sahay ................. A61F 2/30942
128/898

(Continued)

FOREIGN PATENT DOCUMENTS

CN 103492870 A 1/2014
CN 104185446 A 12/2014
(Continued)

OTHER PUBLICATIONS

Thrun, Sebastian et al., "A Probabilistic Approach to Concurrent Mapping and Localization for Mobile Robots", Machine Learning and Autonomous Robots (joint issue), 1998, pp. 1-25, vol. 31, Issue 1-3, © 1998 Kluwer Academic Publishers, Boston; DOI: 10.1023/A:1007436523611.

(Continued)

*Primary Examiner* — Ellen C Hammond
*Assistant Examiner* — Tara Rose E Carter
(74) *Attorney, Agent, or Firm* — Blue Filament Law PLLC

(57) ABSTRACT

A system and process is provided for dynamically positioning or repositioning a robot in a surgical context based on workspace and task requirements, manipulator requirements, or user preferences to execute a surgical plan. The (Continued)

system and method accurately determines and indicates an optimal position for a robot with respect to a patient's anatomy before or during a surgical procedure. Optimal positions for a robot are intuitively indicated to a user, surgical procedures can illustratively include surgery to the knee joint, hip joint, spine, shoulder joint, elbow joint, ankle joint, jaw, a tumor site, joints of the hand or foot, and other appropriate surgical sites.

16 Claims, 4 Drawing Sheets

(51) Int. Cl.
    A61B 34/00    (2016.01)
    A61B 34/30    (2016.01)
    A61B 34/10    (2016.01)
    A61B 90/00    (2016.01)
    A61B 90/50    (2016.01)
(52) U.S. Cl.
    CPC .............. A61B 34/25 (2016.02); A61B 34/30
        (2016.02); A61B 90/39 (2016.02); A61B
        2034/105 (2016.02); A61B 2034/2048
        (2016.02); A61B 2034/2055 (2016.02); A61B
        2034/2057 (2016.02); A61B 2034/2068
        (2016.02); A61B 2034/254 (2016.02); A61B
        2090/368 (2016.02); A61B 2090/3945
        (2016.02); A61B 2090/3983 (2016.02); A61B
        2090/502 (2016.02)
(58) Field of Classification Search
    CPC ............ A61B 2034/304; A61B 6/5205; A61B
        6/0407; A61B 6/467; A61B 6/466; A61B
        6/4441; A61B 90/39; A61B 90/06; A61B
        90/37
    See application file for complete search history.

(56) References Cited

U.S. PATENT DOCUMENTS

| | | | |
|---|---|---|---|
| 6,033,415 A | 3/2000 | Mittelstadt et al. | |
| 6,061,644 A | 5/2000 | Leis | |
| 6,322,567 B1 | 11/2001 | Mittelstadt et al. | |
| 6,430,434 B1 | 8/2002 | Mittelstadt | |
| 7,043,961 B2 | 5/2006 | Pandey et al. | |
| 7,206,626 B2 | 4/2007 | Quaid, III | |
| 8,219,177 B2* | 7/2012 | Smith | A61B 5/06 600/411 |
| 8,287,522 B2 | 10/2012 | Moses et al. | |
| 8,935,005 B2 | 1/2015 | Rosenstein et al. | |
| 9,498,231 B2* | 11/2016 | Haider | A61B 17/1703 |
| 10,136,948 B2 | 11/2018 | Jensen | |
| 2006/0142657 A1* | 6/2006 | Quaid | A61B 17/1703 600/424 |
| 2009/0192519 A1* | 7/2009 | Omori | A61B 34/30 606/130 |
| 2010/0198218 A1 | 8/2010 | Manzo | |
| 2013/0172905 A1 | 7/2013 | Iorgulescu et al. | |
| 2013/0211419 A1 | 8/2013 | Jensen | |
| 2013/0261446 A1* | 10/2013 | Paladini | A61B 5/0064 600/436 |
| 2014/0039517 A1 | 2/2014 | Bowling et al. | |
| 2014/0276855 A1 | 9/2014 | De La Barrera et al. | |
| 2015/0100066 A1* | 4/2015 | Kostrzewski | A61B 34/30 606/130 |
| 2015/0196365 A1 | 7/2015 | Kostrzewski et al. | |
| 2015/0366624 A1 | 12/2015 | Kostrzewski et al. | |
| 2016/0008078 A1 | 1/2016 | Azizian et al. | |
| 2018/0014888 A1 | 1/2018 | Bonny et al. | |
| 2018/0065252 A1 | 3/2018 | Tabandeh et al. | |

FOREIGN PATENT DOCUMENTS

| | | |
|---|---|---|
| CN | 104434149 A | 3/2015 |
| CN | 105147393 A | 12/2015 |
| ES | 2392059 A1 | 12/2012 |
| WO | 2003077101 A3 | 9/2003 |
| WO | 2009092164 A1 | 7/2009 |
| WO | 2014/198784 A1 | 12/2014 |

OTHER PUBLICATIONS

Fox, Dieter et al., "Markov Localization for Mobile Robots in Dynamic Environments", Journal of Artificial Intelligence Research, 1999, pp. 391-427, vol. 11, © 1999 AI Access Foundation and Morgan Kaufmann Publishers; DOI: 10.1613/jair.616.

Schwier, Andrea et al., "VR-Map: A New Device for Patient Registration and Optimal Robot Positioning", CURAC, 2010, Institute of Robotics and Mechatronics, German Aerospace Center (DLR), Wessling, Germany, 4 pages, https://www.robotic.dir.de/fileadmin/robotic/konietschke/Publications/CURAC_2010_Schwier et_al.pdf.

International Search Report dated Jun. 9, 2017 for International Application No. PCT/US2017/019746 filed Feb. 27, 2017.

Supplementary EESR and Opinion dated Sep. 19, 2019, issued in co-pending EP Patent Appln. No. EP17757426.

1st Office Action issued in Chinese Patent Appln. No. 201780013176. 2, dated Jul. 3, 2020.

* cited by examiner

METHOD AND SYSTEM FOR GUIDING USER POSITIONING OF A ROBOT

CROSS-REFERENCE TO RELATED APPLICATION

This application claims priority of U.S. Provisional Patent Application Ser. No. 62/300,234 filed Feb. 26, 2016, which is incorporated herein by reference.

FIELD OF THE INVENTION

The present invention in general relates to the field of robotic and computer assisted surgery; and in particular, to a new and useful process and system for dynamically positioning a surgical robot based on workspace and task requirements.

BACKGROUND OF THE INVENTION

Robotic surgical procedures have become a preferred medical technique for many complex surgeries that require a high level of precision. Computer assisted surgical devices such as robots are gaining popularity as a tool to pre-operatively plan and precisely execute the plan to ensure an accurate final position and orientation of a prosthetic within a patient's bone that can improve long term clinical outcomes and increase the survival rate of a prosthesis compared to a manually performed surgery. In general, the computer assisted surgical systems include two components, an interactive pre-operative planning software program and a computer assisted surgical device that utilizes the pre-operative data from the software to assist the surgeon in precisely executing the procedure.

Conventional interactive pre-operative planning software generates a three dimensional (3-D) model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to place the components of a desired prosthesis to the 3-D model of the bony anatomy to designate the best fit, position, and orientation of the prosthesis to the bone. The final surgical plan data may include instructions for a surgical device, such as a set of points in a cut-file or a set of haptic virtual boundaries, to precisely modify a volume of tissue or assist a surgeon in modifying the tissue to achieve the goals of the plan.

Common surgical procedures performed with robotic assistance are total and partial joint replacements. Joint replacement (also called primary joint arthroplasty) is a surgical procedure in which the articulating surfaces of a joint are replaced with prosthetic components. Joint replacement has become a successful procedure, especially for hips, knees, shoulders, and ankles, and allows people to restore functionality while greatly reducing pain associated with osteoarthritis. Commercial robotic systems for executing total and partial joint replacements include the TSolution One™ Surgical System (THINK Surgical Inc., Fremont, Calif.) and the RIO® Interactive Orthopedic System (Stryker-Mako, Ft. Lauderdale, Fla.). Examples of these robotic systems are described in greater detail in U.S. Pat. Nos. 5,086,401 and 7,206,626.

To perform a joint replacement procedure with a robotic system, the correct positioning of the robot with respect to the patient is critical. For example, with the TSolution One™ Surgical System, a moveable base is currently manually maneuvered next to the target anatomy and fixed into a position using a braking mechanism on the moveable base. A fixator arm is then secured to the bone to fix the bone to the system. Subsequently, the position and orientation (POSE) of the bone are registered to the surgical plan and to the system using a tracking mechanism (e.g., an optical tracking system, a mechanical tracking system). After registration, the robotic system determines if an end-effector tool of the robot can perform a surgical task (i.e., execute the surgical plan) on the anatomy. All of the points or boundaries in the task should be within the workspace of the robot, and hence all the points or boundaries should be reachable by the robot. In other words, the end-effector tool needs to reach all of the points or boundaries designated in the surgical plan with respect to the target anatomy.

The primary problem with the current approach is limited a priori information for the optimal position for the robot base prior to approaching the patient with the robot. Therefore, if the robotic system determines the end-effector tool is unable to perform the surgical task with the base already fixed relative to the patient, the base may need to be repositioned and the bone re-registered. In addition, there is no guarantee that the new position for the base is suitable to perform the surgical task. There is also the possibility that when the position of the base with respect to the anatomy changes, this causes the designated points or boundaries to also change within the workspace of the robot. Some of these points or boundaries may be pushed out of the workspace and become unreachable. Sometimes a change in the height of the robot in terms of the base height is sufficient (i.e., an upward or downward translation of the manipulator arm), while in other cases the position of the base needs to be completely re-positioned with respect to the anatomy. This becomes more important in cases of total knee arthroplasty (TKA) where the end-effector tool is often reoriented several times. All of these problems can greatly increase the time needed to perform the operation, especially if the target anatomy needs to be fixed to the robotic system (e.g., see robotic-bone fixation as described in U.S. Pat. No. 5,086, 401).

Computer aid has also been limited in many instances to the execution of a surgical plan with cut parameters that are based on limited input for instance input that is limited to the dimensions of a cutting cavity correlating to a particular prosthesis, and the position of the prosthesis in a bone model. As a result, a surgeon must still manually contend with soft tissue issues. In addition, there are other parameters of the robotic system that should be addressed prior to positioning the base. This may include how the manipulator arm articulates to perform the task and whether any of those articulations may cause a fault or error such as a singularity fault. There may be preferences by a surgeon or surgical team to have particular access points or corridors to the operating site with which the robotic system may otherwise interfere. If an optical tracking system is present, the base should be positioned to maintain the line-of-sight between any tracking markers and the tracking system throughout the entire procedure. By simply guessing a position for the base next to the anatomy, these parameters will not be optimal.

Finally, once an optimal position for the base has been determined, that position needs to be conveyed to the surgical team in an intuitive and accurate manner. A few millimeters in base position could have an effect on the surgical procedure workflow and the overall surgical time.

Thus, there exists a need for a system and method to optimally position or reposition a robotic system with respect to a patient's anatomy according to task requirements, manipulator requirements, or user preferences to execute a surgical plan. There is a further need to intuitively indicate the optimal position for the robotic system to a user.

SUMMARY OF THE INVENTION

A process is provided for positioning a robot in an operating room containing a surgical table, the robot having a moveable base, a manipulator arm, and an end effector tool. The process includes: evaluating an initial position of the moveable base in the operating room, the robot having a programmed surgical plan; moving the moveable base from the initial position towards the surgical table with collision avoidance mobility software to a first determined position; stopping the moveable base; and engaging the manipulator arm and the end effector tool.

A process is provided for positioning a robot in an operating room containing a surgical table with a bone thereon, the robot having a moveable base, a manipulator arm, an end effector tool attached to the manipulator arm, and a computer containing a surgical plan program and hardware to communicate the plan to the manipulator arm. The process includes assuming a certain position and orientation (POSE) with the manipulator arm to form an axis of the end effector tool that represents a desired position of an axis of the bone, and moving the moveable base or the registered bone to approximately align the axis of the registered bone and the axis of the end effector tool.

A process is provided for positioning a robot in an operating room containing a surgical table, the robot having a moveable base, a manipulator arm, and an end effector tool. The process includes: determining a first position of the moveable base in the operating room, the robot having a programmed surgical plan; moving the moveable base from an initial position towards the surgical table to the determined first position; stopping the moveable base; and engaging the manipulator arm and the end effector tool.

A robotic surgical system operating on a floor is provided. The robotic surgical system includes a computer assisted surgical robot having a base, an end effector tool projecting from the robot, fiducial marker arrays and an optical tracking system for tracking or navigating the end effector relative to a subject bone. The surgical system further includes a surgical plan of operations to be performed on the subject bone, and a laser, a 2-D image, or holographic image projector to project an image of a desired position for the base of the robot on the floor to comply with at least one operation of the surgical plan of operations.

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE INVENTION

The present invention has utility as a system and process for dynamically positioning or repositioning a robot in a surgical context based on workspace and task requirements, manipulator requirements, or user preferences. Embodiments of the inventive system and method accurately determine and indicate an optimal position for a robot with respect to a patient's anatomy before or during a surgical procedure.

The following description of the preferred embodiments of the invention is not intended to limit the invention to these preferred embodiments, but rather to enable any person skilled in the art to make and use this invention. The invention described herein illustratively uses total knee arthroplasty (TKA) as an example. Although total knee arthroplasty is one procedure that can benefit from the disclosed embodiments other surgical procedures can illustratively include surgery to the knee joint, hip joint, spine, shoulder joint, elbow joint, ankle joint, jaw, a tumor site, joints of the hand or foot, and other appropriate surgical sites.

Figure 1:
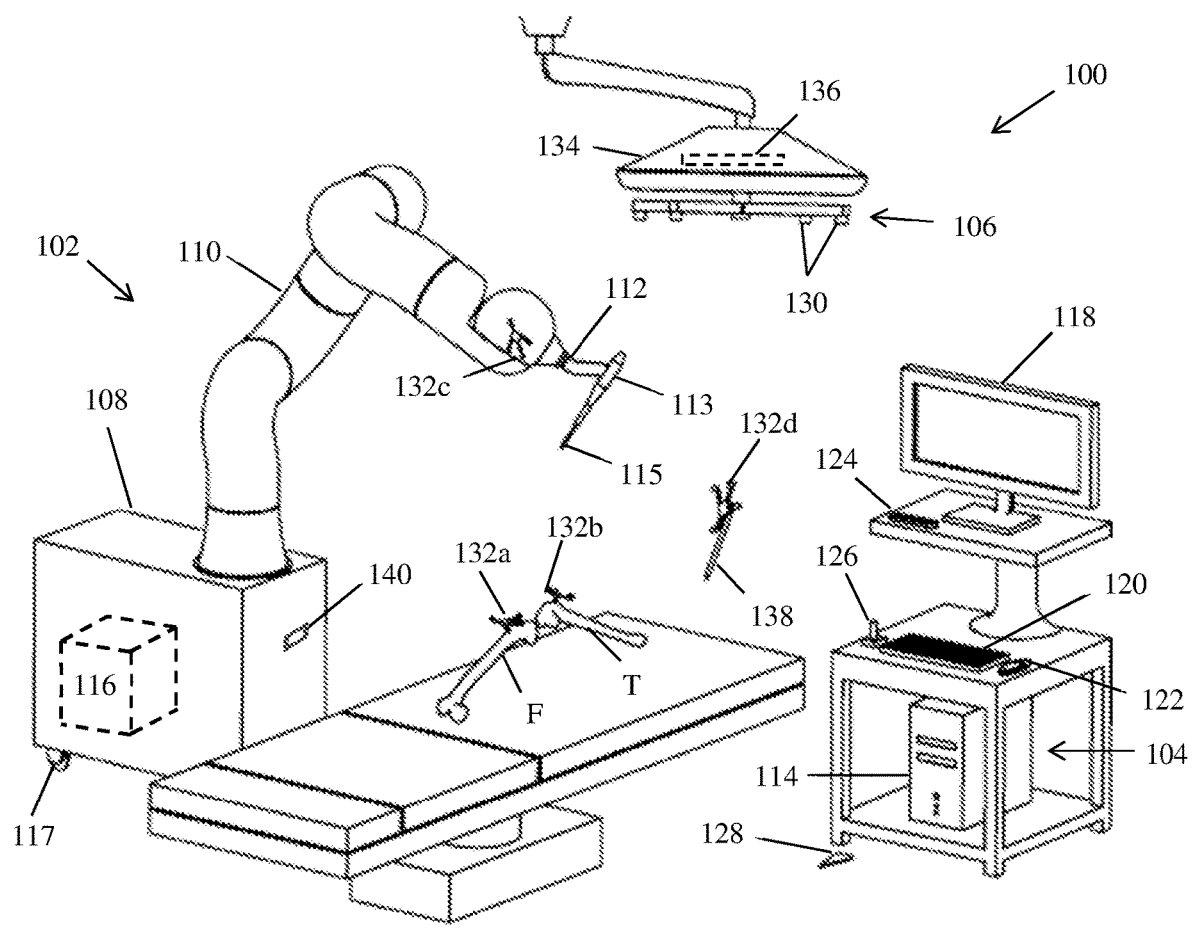
FIG. 1 depicts an inventive operating room with a surgical system having a robotic computer-assisted device, a computing system, and a tracking system, where the robotic device has a positioning indicator to provide a user with an indication of an optimal position for the robot with respect to a patient's anatomy in accordance with embodiments of the invention.

With reference to the figures, FIG. 1 illustrates an embodiment of a surgical system and operating room (OR) for a robotic assisted surgical procedure. The surgical system 100 generally includes a surgical robot 102, a computing system 104, and a tracking system 106.

The surgical robot 102 includes a moveable base 108, a manipulator arm 110 connected to the movable base 108, an end-effector flange 112 located at a distal end of the manipulator arm 110, and an end-effector tool 113 having a tool tip 115, where the tool 113z is removably attached to the end-effector flange 112. The moveable base 108 may include a set of wheels 117 to maneuver the base 108, which may be fixed into position using a braking mechanism such as a hydraulic brake. The manipulator arm 110 includes various joints and links that provide control or motion in various degrees of freedom. The joints may be prismatic, revolute, or a combination thereof. The tool 113 may be any device to contact or perform work on the patient's anatomy including for example a burr, a saw, an end-mill, a cutter, a laser ablation device, forceps, an endoscope, electrocautery device, a drill, a pin driver, a reamer, an ultrasonic horn, a catheter guide, or a probe. The tool 113 and manipulator arm 110 are controlled by commands from the computing system 104.

The computing system 104 generally includes a planning computer 114 having a processor; a device computer 116 having a processor; a tracking computer 136 having a processor; and peripheral devices. The planning computer 114, device computer 116, and tracking computer 136, may be separate entities, single units, or combinations thereof depending on the surgical system. The peripheral devices allow a user to interface with the surgical system components and may include: one or more user-interfaces, such as a display or monitor 118; and user-input mechanisms, such as a keyboard 120, mouse 122, pendent 124, joystick 126, foot pedal 128, or the monitor 118 may have touchscreen capabilities.

The planning computer 114 contains hardware (e.g., processors, controllers, and memory), software, data and utilities that are preferably dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan may include the three-dimensional bone models having points to facilitate registration, patient identification information, workflow instructions, and operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. The data generated from the planning computer 114 may be transferred to the device computer 116 and/or tracking computer 136 through a wired or wirelessly connection in the operating room (OR); or transferred via a non-transient data storage medium (e.g., a compact disc (CD), a portable universal serial bus (USB) drive) if the planning computer 114 is located outside the OR.

The device computer 116 may be housed in the moveable base 108 and contain hardware, software, data and utilities that are preferably dedicated to the operation of the surgical device 102. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, and utilizing position and orientation (POSE) data from the tracking system 106.

Figure 2:
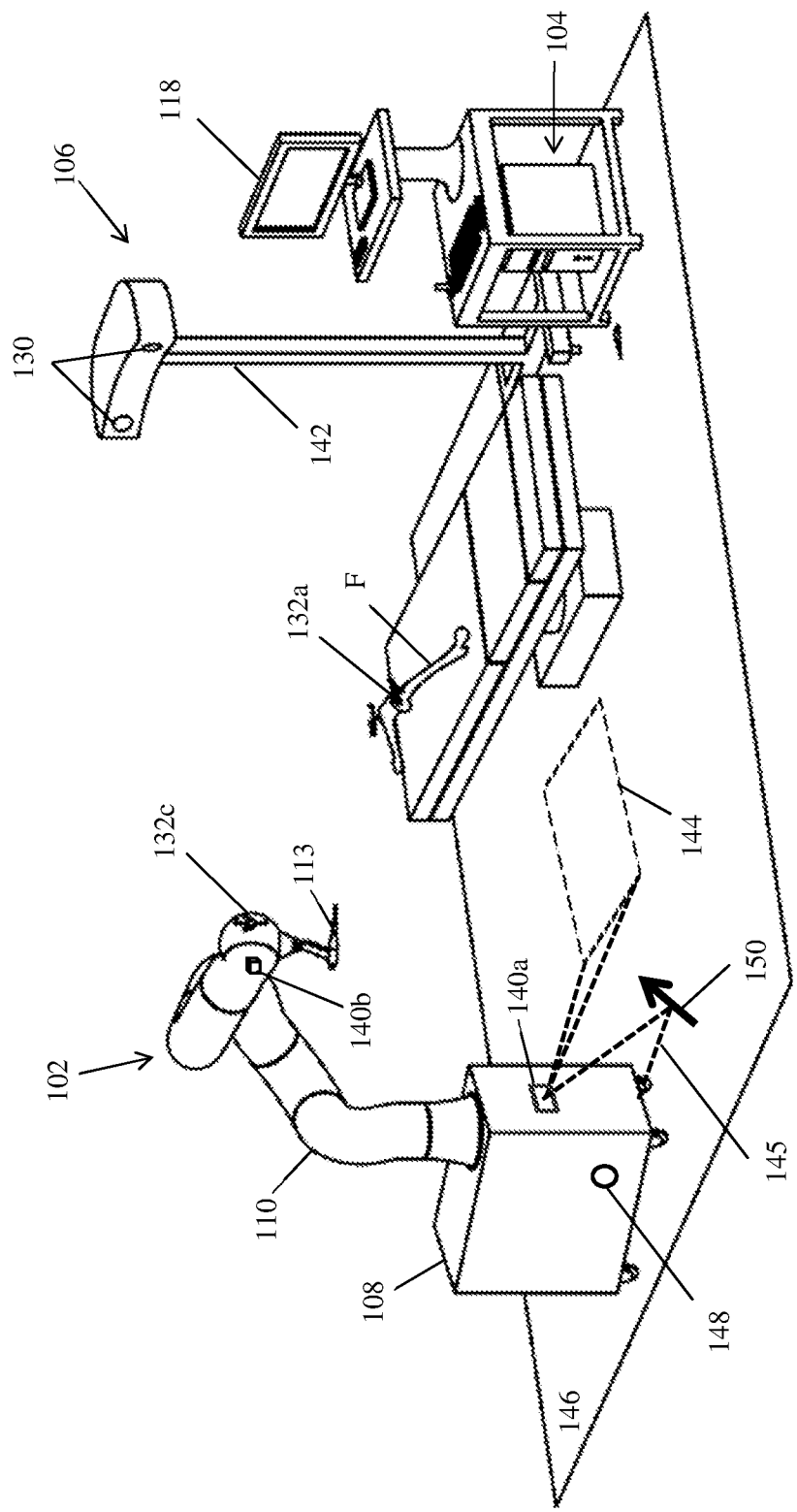
FIG. 2 illustratively depicts an inventive operating room with a robotic computer-assisted device having an indicator that is indicating an optimal position for the base, and other sensors for guiding the base of the device to the optimal position in accordance with embodiments of the invention.

The tracking system 106 of the surgical system 100 includes two or more optical receivers 130 to detect the position of fiducial markers (e.g., retroreflective spheres, active light emitting diodes (LEDs)) uniquely arranged on rigid bodies. The fiducial markers arranged on a rigid body are collectively referred to as a fiducial marker array 132, where each fiducial marker array 132 has a unique arrangement of fiducial markers, or a unique transmitting wavelength/frequency if the markers are active LEDs. An example of an optical tracking system is described in U.S. Pat. No. 6,061,644. The tracking system 106 may be built into a surgical light 134, located on a boom, a stand 142 (as shown in FIG. 2), or built into the walls or ceilings of the OR. The tracking system 106 may include tracking hardware 136, software, data and utilities to determine the POSE of objects (e.g., femur F, tibia T, surgical device 102) in a local or global coordinate frame. The POSE of the objects is collectively referred to herein as POSE data, where this POSE data may be communicated to the device computer 116 through a wired or wireless connection. Alternatively, the device computer 116 may determine the POSE data using the position of the fiducial markers detected from the optical receivers 130 directly.

The POSE data is determined using the position data detected from the optical receivers 130 and operations/processes such as image processing, image filtering, triangulation algorithms, geometric relationship processing, registration algorithms, calibration algorithms, and coordinate transformation processing. For example, the POSE of a digitizer probe 138 with an attached probe fiducial marker array 132d may be calibrated such that the probe tip is continuously known as described in U.S. Pat. No. 7,043,961. The POSE of the tip 115 or tool axis of the end effector tool 113 may be known with respect to a device fiducial marker array 132c using a calibration method as described in U.S. Prov. Pat. App. 62/128,857. The device fiducial marker 132c is depicted on the manipulator arm 110 but may also be positioned on the base 108 or the tool 114. Registration algorithms may be executed to determine the POSE and/or coordinate transforms between a bone (e.g., femur F, tibia T), a bone fiducial marker array (132a, 132b), a surgical plan, and any combination thereof using registration methods known in the art such as those described in U.S. Pat. Nos. 6,033,415, and 8,287,522.

Upon assembly of the device tracking array 132c to the surgical robot 102 prior to surgery, the POSE's of the coordinate systems, 132c and 113, are fixed relative to each other and stored in memory to accurately track the end effector tool 113 during the surgery (see for example U.S. Patent Publication 20140039517 A1) relative to the bone anatomy (e.g., femur F, and tibia T). The POSE data may be used by the computing system 104 during the procedure to update the robot and surgical plan coordinate transforms so the surgical robot 102 can accurately execute the surgical plan in the event any bone motion occurs. It should be appreciated that in certain embodiments, other tracking systems may be incorporated with the surgical system 100 such as an electromagnetic field tracking system or a mechanical tracking system. An example of a mechanical tracking system is described in U.S. Pat. No. 6,322,567.

Due to the criticality of positioning the base 108 with respect to the anatomy as described above, the optimal position for the robot may be determined using several algorithms which heavily rely on global and local optimization algorithms. The optimization algorithms may use a kinematic model of the robotic system, and a known POSE of the patient's anatomy (as determined by registering the surgical plan to the bone prior to approaching the patient with the robot) to determine an optimal position for the base to achieve the desired reachability within the operative volume such as the points in the cut file, a set of boundaries, or a set of drill holes or planar cuts, defined in the surgical plan. The optimization algorithms may also include additional constraints for determining the optimal position. The constraints may include manipulator requirements such as the avoidance of a singularity, a joint limit, or a collision of the manipulator arm while executing the surgical plan. The constraints may include line-of-sight considerations where the location of a fiducial marker array relative to the tracking system may be optimized for a particular base position or manipulator arm configuration. The constraints may further include user's preferences for the position of the base, to provide the user with particular access points or corridors to the operational site, where the robot is still capable of executing the surgical plan. The preferences may also include how the base should be oriented to easily grasp and wield the manipulator arm or end-effector tool if a passive or haptic surgical robot is used. The algorithm constraints may also include patient factors such as the patient's body mass index (BMI), the operating side (e.g., left or right femur), or amount of exposure of the targeted anatomy. The user's preferences and patient factor constraints may be defined in the operating room or in the surgical plan and loaded into the tracking system 106 or computing system 104 prior to running the optimization algorithm. Simulations of the manipulator joints and links may also be performed in conjunction with or in lieu of the constrained optimization algorithms by using the kinematic model at various potential base positions relative to the anatomy/plan, until an optimal position for the base is found to accommodate these manipulator requirements. Ultimately, the output of the optimization algorithms and/or simulations, that is the optimal position of the base, may then be used by the operating room (OR) staff to position or re-position the robot with respect to the anatomy.

It should be noted that in certain embodiments, the position and orientation of a targeted bone with respect to a certain world coordinate frame is required prior to positioning the robotic system. For example, if a tracking system is present, the current position of the bone to the tracking system may be determined using a partial or full registration process with the digitizer probe 138, where the surgical plan data may be uploaded to the tracking system 106 prior to the registration. In a particular embodiment, a user may plan the procedure intra-operatively and use bone-morphing registration techniques (commonly used in imageless computer-aided procedures) to determine the POSE of the bone with respect to a world coordinate frame. With the bone known in a world coordinate frame, the optimal position and orientation for the base of the robot with respect to the bone is determined using one of the optimization algorithms and methods described above. Once the optimal position has been determined, the position needs to be conveyed to the OR staff in an intuitive and accurate manner.

In an inventive embodiment shown in FIG. 2, a laser, a 2-D image, or holographic image 144 may be used to display the optimal position for the base 108 of the robot 102 on the floor 146. The indicator may indicate the position in either absolute coordinate space or relative to the current position of the robot 102. The absolute indicator shows the optimal position of the robot in the OR by projecting the footprint 144 of the robot base 108 on the floor 146. As the robot moves toward the location of the optimal position, the projected image 144 may update so the footprint 144 remains at the optimal position in absolute coordinate space. The relative indicator shows the direction that the base 108 should be moved or rotated towards, to reach the optimal position, such as the indicating arrow 150. The projectors 140, such as pico projectors, are mounted, for example, on the base 108 of the robot 102 or on the manipulator arm 110. The projector 140 may also be mounted underneath the base 108 so the image 144 can be continually updated as the base 108 moves on top of the image 144 (e.g., projection emanating from the bottom of the base at 145). For this embodiment, in addition to the position of the bone (e.g., femur F, or tibia T), the position of the base 108 of the robot 102 is also needed. This position of the base 108 of the robot 102 can be determined by exposing the device fiducial marker array 132c attached to the arm of the robot to the tracking system 106.

In an inventive embodiment, the robot base 108 may be equipped with laser distance measurement sensors (LIDARS) 148 and/or cameras to utilize machine vision to position the robot 102. The base 108 uses autonomous robot algorithms to safely navigate itself to the optimal position while avoiding collisions with the staff and objects in the OR. The position of the base 108 of the robot 102 is needed for this embodiment, which may be determined with a tracking system 106, or may be determined with the on-board equipment (e.g., measurement sensors, cameras) and mapping software loaded on the device computer 116. It is appreciated that compared to a robot moving in a dynamic environment, the OR is a comparatively controlled environment and readily mapped. An autonomous robotic base 108 can move automatically with resort to a powered drive wheel system that includes navigation modules performed functions of mapping, localization, collision avoidance, and path planning. Variations in patient size and potential interference with anesthesia that might lead to a serious collision or interference with the procedure are simultaneously avoided by creating an exclusion zone around the head portion of the OR table 135 that is depicted as the two small sections of the table 135 in FIGS. 1 and 2.

In certain inventive embodiments, an occupancy map is learned to combine the concurrent mapping and localization problem as a maximum likelihood estimation problem, in which one seeks to determine a most likely map given the data. Likelihood maximization takes into account the consistency of the odometry as small errors are more likely than large ones, and discounts perceptual consistency, as detailed in S. Thrun, D. Fox, and W. Burgard. A probabilistic approach to concurrent mapping and localization for mobile robots. Machine Learning, 31, 1998. In contrast to robots operating in an open space, the surgical robot base 108 functions in a controlled and predictable environment of an OR. A controlled environment allows an inventive robot to operate within the assumption of Markov localization D. Fox, W. Burgard, and S. Thrun, Markov Localization for Mobile Robots in Dynamic Environments, Journal of Artificial Intelligence Research 11 (1999) 391-427. It uses Bayes rule to incorporate sensor readings and it uses convolution to incorporate robot motion. Initially, the robot does now know its pose; thus, $P\ r(\xi(0))$ is distributed uniformly. After incorporating one sensor reading (e.g., RFID, laser or camera) according to the update rule (1), $P\ r(\xi(1))$ is distributed. After moving forward, and after incorporating another sensor reading, the final distribution $P\ r(\xi(2))$ is centered around the correct pose raw proximity sensor readings along with a desired robot final location, the path and velocity of the robot are calculated based on preselected constraints that include the robot must always be able to come to a full stop before impact while contending with dynamic constrains (e.g., torque limits). Soft constraints are used to balance the program desire to move directly towards the final location by the fastest and shortest route. In combination, these constraints ensure safe and smooth local navigation.

The path planner computes paths from one position of surgical action to another. The collision avoidance mobility software allows the robot base 108 to maneuver in the OR. In some inventive embodiments, beyond automatic braking capabilities to avoid collision, an alarm is provided in the event that a transit trajectory is in process that can lead to a collision, whether under autonomous or manual control.

Figure 3:
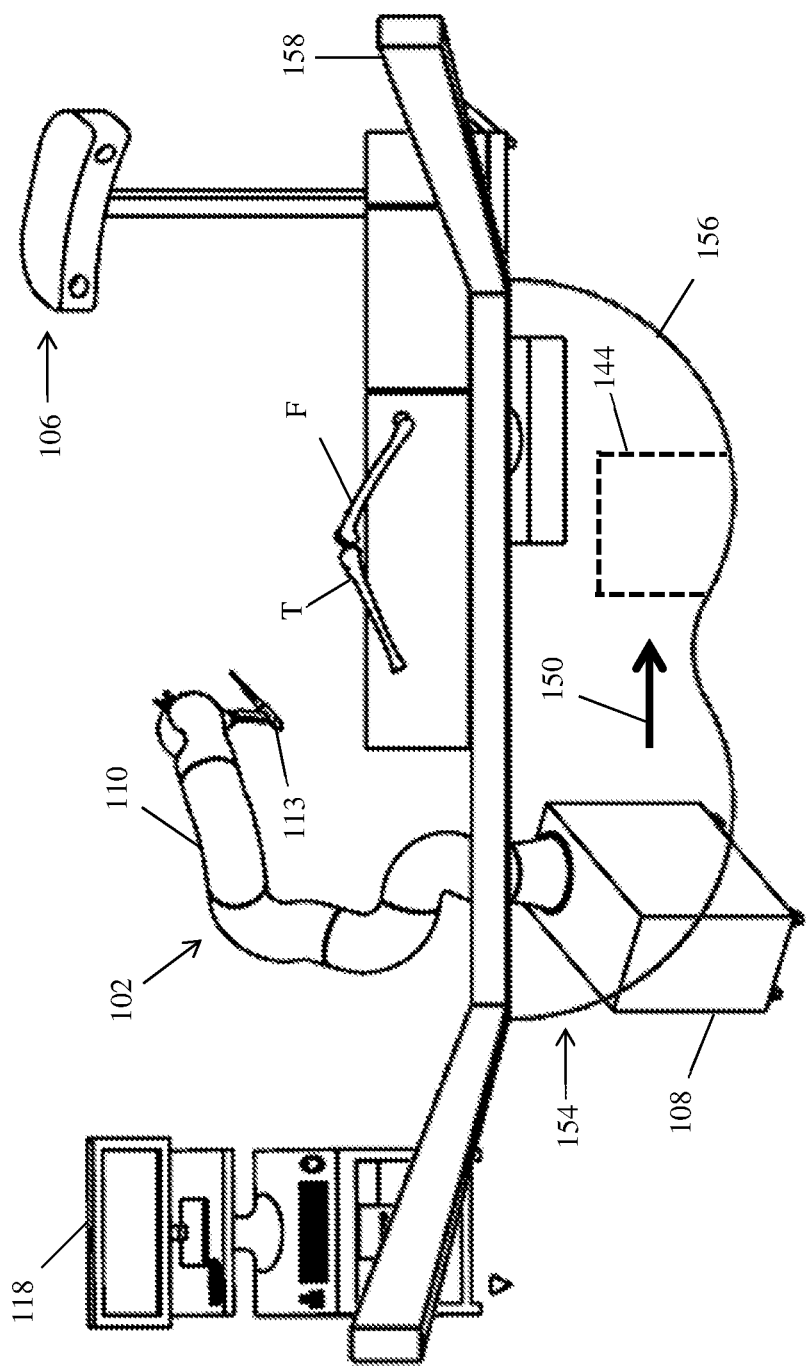
FIG. 3 illustratively depicts the use of an augmented reality device for displaying the optimal position for a base of a robotic surgical device in accordance with embodiments of the invention.

In a specific inventive embodiment, with reference to FIG. 3, an augmented reality device 154 illustratively including, but not limited to Google glass, Microsoft's holo lens, or ODG's glasses is used to display the optimal position of the robot 102 within the OR. A silhouette of the robot base 144 at the optimal position may be shown in the field of view 156 of the augmented reality device 154. A relative arrow indicator 150 may also be shown in the field of view 156. The POSE of the augmented reality device 154 may be collected either from the internal sensors (inertial measurement unit (IMU), compass, etc.) of the augmented reality device 158 or from a augment device fiducial marker array 132d mounted on the reality device 154 that can be seen by the tracking system 106.

Figure 4:
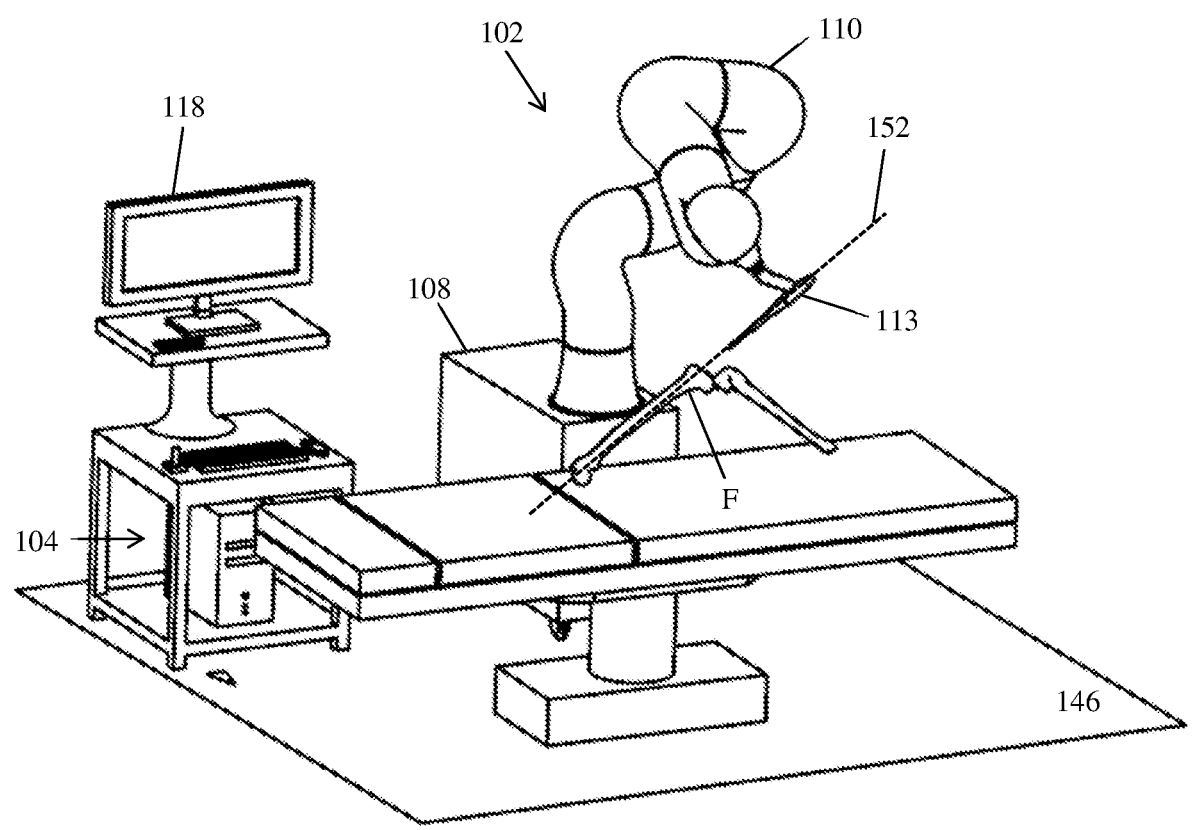
FIG. 4 illustratively depicts an inventive operating room with a robotic computer-assisted device without any additional indicators or sensors, wherein the robotic base is guided to an optimal position according to the orientation of the robot manipulator arm in accordance with embodiments of the invention.

In a specific inventive embodiment, with reference to FIG. 4, the manipulator arm 110 may assume a certain POSE which represents the desired position of the bone axis with respect to the axis of the tool 113. The user may then move the base 108 of the robot 102 such that the bone (e.g., femur F, or tibia T) is roughly aligned with the axis of the tool 113 by either positioning the base 108 of the robot 102 or the patient anatomy (i.e. aligning the tool axis and bone axis shown along axis 152). This method does not require a tracking system 106 or the registration information and only depends on the analyses performed on the surgical plan to assume the certain POSE. In other words, the robot 102 assumes a POSE that is desired regardless of the current position of the patient. In this embodiment, the initial POSE of the manipulator arm 110 may take into account the manipulator requirements, surgeon preferences, and patient factors. If the manipulator arm 110 has greater than 6 degrees of freedom (DOF), the redundant degrees of freedom provides greater flexibility to achieve the manipulator requirements, surgeon preferences, and patient factors.

In an inventive embodiment the registration algorithm may be used to determine a suitable position for the robot 102, and then the robot 102 assumes a pose which includes the correct base height. The input to this method could be the full registration information including the position and orientation of the patient or at a minimum could be landmarks of the anatomy such as the top of the knee in case of a knee procedure.

A graphical user interface (GUI) method is also provided in which a display on monitor 118 is used to provide the user with positioning information. For example, if the position and orientation of the robot 102 with respect to the bone/patient is known, both the current and optimal position of the robot base 108 with respect to the patient is displayed on a screen. When the base 108 of the robot 102 is moved the screen is updated to provide a visual assist in moving the robot 102 to an optimal position. In an additional embodiment, a side and top view of the bone and the footprint of the base 108 of the robot are displayed, where the color of the bone changes to indicate if the bone is within a reachable part of the workspace, and to show a direction of the movement of the base 108 that would lead to a reachable point in the work space. In a specific embodiment, a target symbol (e.g., crosshairs) is displayed on the GUI. The target symbol may first appear enlarged on the screen and then focuses in to the optimal position for the base as the base is moved to the optimal position.

For fine motions of the robot during the positioning, in an inventive embodiment an elephant trunk method may be used. In the elephant trunk method, a surgeon uses the tool assembly 113 or manipulator arm 110 of the robot 102 as a joystick to move the robot 102. This requires a powered robot base 108 that may be moved by electrical steering. A description of the elephant trunk method is further described in U.S. Prov. Pat. App. No. 62/142,624, which is hereby incorporated by reference.

It should be appreciated that the methods described above may be extended to the reach of a passive digitizer arm attached to a robotic system as described in U.S. Pat. No. 6,033,415 and incorporated herein in its entirety. The optimization algorithms may further determine an optimal position for the digitizer or robotic base 108 such that the digitizer arm complies with any workspace, task, user, or patient requirements.

After the base 108 has been positioned, the tracking system 106 may verify that the base 108 is at an optimal position, or at the very least verify that the the workspace and task requirements are satisfied. The monitor 118 may display a prompt for the user to acknowledge the position of the base 108. In a particular embodiment, the user may want to reposition the base 108 to gain access to particular locations in or around the operating site, or to have a better grip to wield a passive or haptic manipulator arm. The monitor 118 may display the current position of the base 108 with respect to the anatomy. A triad or rotation cursor may be displayed that allows the user to virtually adjust the position of the base on the monitor 118. The tracking system 106 or computing system 104 may provide feedback indicating whether the virtually adjusted position will still accommodate the workspace or task requirements. Therefore, the user has an idea of where the base may be re-positioned before actually moving the base 108. Once a new position has been determined, any of the methods described above may be used to reposition the base 108 of the robot 102.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The foregoing description is illustrative of particular embodiments of the invention, but is not meant to be a limitation upon the practice thereof. The following claims, including all equivalents thereof, are intended to define the scope of the invention.

The invention claimed is:

1. A robotic surgical system operating on a floor comprising:
    a computer assisted surgical robot having a base;
    an end effector tool projecting from said computer-assisted surgical robot;
    fiducial marker arrays and an optical tracking system for tracking or navigating said end effector relative to a subject bone;
    a surgical plan of operations to be performed on the subject bone;
    a laser, a 2-D image, or image projector to project an image of a desired position for the base of said computer-assisted surgical robot on the floor to comply with at least one operation of said surgical plan of operations; and
    a software module for executing an optimization algorithm to determine the desired position using two or more inputs, wherein the inputs are selected from the group consisting of: a position of the subject bone; a position of the at least one operation to be performed on the subject bone; a robot kinematic model; a position of the robot; or a position defined by a user relative to the subject bone.

2. The robotic surgical system of claim 1 wherein the surgical plan of operations includes a cut-file of operations, a virtual boundary constraint of operations, or a graphically navigated set of operations.

3. The robotic surgical system of claim 1 wherein all physical points dictated in said surgical plan of operations are reachable by said end effector tool when the moveable base is positioned at the desired position.

4. The robotic surgical system of claim 1 further comprising a laser distance measurement sensors (LIDARS) and machine vision.

5. The robotic surgical system of claim 1 further comprising an augmented reality device to display the desired position.

6. A robotic surgical system operating on a floor comprising:
- a computer assisted surgical robot having a base;
- an end effector tool projecting from said robot;
- fiducial marker arrays and an optical tracking system for tracking or navigating said end effector relative to a subject bone;
- a surgical plan of operations to be performed on the subject bone;
- a laser, a 2-D image, or image projector to project an image of a desired position for the base of said robot on the floor to comply with at least one operation of said surgical plan of operations; and
- autonomous robot algorithms to navigate the base to the desired position.

7. The robotic surgical system of claim 6 further comprising a software module for executing an optimization algorithm to determine the desired position using two or more inputs, wherein the inputs are selected from the group consisting of: a position of the subject bone; a position of the at least one operation to be performed on the subject bone; a robot kinematic model; a position of the robot; or a position defined by a user relative to the subject bone.

8. The robotic surgical system of claim 6 wherein the surgical plan of operations includes a cut-file of operations, a virtual boundary constraint of operations, or a graphically navigated set of operations.

9. The robotic surgical system of claim 6 wherein all physical points dictated in said surgical plan of operations are reachable by said end effector tool when the moveable base is positioned at the desired position.

10. The robotic surgical system of claim 6 further comprising a laser distance measurement sensors (LIDARS) and machine vision.

11. The robotic surgical system of claim 6 further comprising an augmented reality device to display the desired position.

12. A robotic surgical system operating on a floor comprising:
- a computer assisted surgical robot having a base on a first position on the floor;
- an end effector tool projecting from said computer-assisted surgical robot;
- fiducial marker arrays and an optical tracking system for tracking or navigating said end effector relative to a subject bone;
- a surgical plan of operations to be performed on the subject bone;
- a laser, a 2-D image, or image projector to project an image of a desired second position for the base of said computer-assisted surgical robot, wherein the projected image is on the floor to comply with at least one operation of said surgical plan of operations; and
- a software module for executing an optimization algorithm to determine the desired position using two or more inputs, wherein the inputs are selected from the group consisting of: a position of the subject bone; a position of the at least one operation to be performed on the subject bone; a robot kinematic model; a position of the robot; or a position defined by a user relative to the subject bone.

13. The robotic surgical system of claim 12 wherein the surgical plan of operations includes a cut-file of operations, a virtual boundary constraint of operations, or a graphically navigated set of operations.

14. The robotic surgical system of claim 12 wherein all physical points dictated in said surgical plan of operations are reachable by said end effector tool when the moveable base is positioned at the desired position.

15. The robotic surgical system of claim 12 further comprising a laser distance measurement sensors (LIDARS) and machine vision.

16. The robotic surgical system of claim 12 further comprising an augmented reality device to display the desired position.

* * * * *